(12) United States Patent
Bhattacharyya

(10) Patent No.: US 11,679,197 B2
(45) Date of Patent: Jun. 20, 2023

(54) DEVICE AND METHODS FOR REDUCING PRESSURE IN MUSCLE COMPARTMENTS

(71) Applicant: Timothy Bhattacharyya, Chevy Chase, MD (US)

(72) Inventor: Timothy Bhattacharyya, Chevy Chase, MD (US)

(*) Notice: Subject to any disclaimer, the term of this patent is extended or adjusted under 35 U.S.C. 154(b) by 432 days.

(21) Appl. No.: 16/893,896

(22) Filed: Jun. 5, 2020

(65) Prior Publication Data
US 2021/0379254 A1    Dec. 9, 2021

(51) Int. Cl.
*A61M 1/00* (2006.01)

(52) U.S. Cl.
CPC ............... *A61M 1/84* (2021.05); *A61M 1/76* (2021.05); *A61M 2205/0238* (2013.01); *A61M 2205/32* (2013.01); *A61M 2210/083* (2013.01); *A61M 2210/086* (2013.01)

(58) Field of Classification Search
CPC .. A61M 1/84; A61M 1/76; A61M 2205/0238; A61M 2205/32; A61M 2210/083; A61M 2210/086; A61M 1/64; A61M 1/00; A61M 1/0023; A61M 1/90; A61M 1/91; A61M 1/92; A61M 1/94; A61M 1/95; A61M 1/96; A61M 1/98
See application file for complete search history.

(56) References Cited

U.S. PATENT DOCUMENTS

| 8,388,584 | B2 | 3/2013 | Odland |
| 2012/0172791 | A1 | 7/2012 | Odland |
| 2016/0367747 | A1* | 12/2016 | Loske ............... A61M 1/772 |
| 2017/0128272 | A1* | 5/2017 | Wu .................. A61M 1/915 |

* cited by examiner

*Primary Examiner* — Amber R Stiles
*Assistant Examiner* — Nelson Louis Alvarado, Jr.
(74) *Attorney, Agent, or Firm* — United IP Counselors, LLC (57) ABSTRACT

Devices and methods for controlling intracompartmental pressure in muscle compartments and, potentially, reducing the incidence of compartment syndrome are disclosed. A device according the invention is a thin, elongate member with an outer layer. The device has a proximal end, which has a coupling constructed and adapted to connect with tubing, and a distal end. The outer layer is at least somewhat permeable to liquids and to cells, either by way of perforations along its length or because of its natural properties. Within and encased by the outer layer lies a core, also porous, and typically an open-celled foam. The core is compressible under the range of suction pressures typically applied in medical contexts. A guide wire may initially be present in the device to aid in its placement. Methods for making such devices, especially on an ad hoc basis, are also disclosed.

16 Claims, 7 Drawing Sheets

DEVICE AND METHODS FOR REDUCING PRESSURE IN MUSCLE COMPARTMENTS

TECHNICAL FIELD

The invention relates to surgical devices, and more particularly, to a compressible suction device for pressure relief in muscular compartments and methods for treating compartment syndrome.

BACKGROUND

Within the human body, a tough sheathing of connective tissue, called fascia, surrounds most skeletal muscles, separating and protecting the muscles from other bodily organs, and forming compartments around the muscles. For example, in the human lower leg, four muscular compartments are formed, surrounding the tibia and fibula.

The fascia sheathe the muscles tightly, leaving little extra room in the muscular compartments. When the pressure in a muscle compartment rises, due to bleeding, swelling of the muscles, or other causes, the rise in pressure can disrupt blood flow to the muscles, a condition called compartment syndrome. The typical treatment, an emergency fasciotomy, involves cutting the fascia to relieve pressure in the muscle compartment, and requires the surgeon to make long, deep, difficult-to-close incisions in the affected limb.

Compartment syndrome is a devastating disease. The onset is insidious, the signs are often unclear, the complications are disastrous, and the treatment is disfiguring. Surgeons are well aware that all patients with a fracture in the tibia can develop compartment syndrome, particularly young men, and that compartment syndrome in the upper limbs is also possible. Malpractice claims regarding compartment syndrome are frequent. Many studies have focused on early diagnosis, but what is really needed is prevention.

BRIEF SUMMARY

Aspects of the invention relate to devices and methods for controlling intracompartmental pressure in muscle compartments and, potentially, reducing the incidence of compartment syndrome.

A device according to one aspect of the invention is a thin, elongate member with an outer layer. The device has a proximal end, which has a coupling constructed and adapted to connect with tubing, and a distal end. The outer layer is at least somewhat permeable to liquids and to cells, either by way of perforations along its length or because of its natural properties. Within and encased by the outer layer lies a core, also porous, and typically an open-celled foam. The core is compressible under the range of suction pressures typically applied in medical contexts. A guide wire may initially be present in the device to aid in its placement.

A method according to another aspect of the invention involves placing devices such as the one described above in the muscular compartments in patients at high risk of developing compartment syndrome. The devices would be surgically placed in one or more affected muscular compartments such that they span the lengths of the compartments, usually once a surgical procedure, such as a procedure to repair a fracture, is complete. Once placed, suction would be connected to the couplings of the devices. The devices would be left in the patient, typically until the risk of compartment syndrome has passed, and then removed. Removal would typically take place without the need for an operating room.

Yet another aspect of the invention relates to the manufacture, and particularly, the ad hoc manufacture of such devices. In a method according to this embodiment of the invention, a device in accordance with the description above is manufactured by the surgeon by cutting an appropriate section of a foam sponge and placing it inside a perforated coating, such as a perforated Penrose drain. The distal end of the device is cut to appropriate length, sealed, and the device is placed.

Other aspects, features, and advantages of the invention will be set forth in the description that follows.

BRIEF DESCRIPTION OF THE DRAWING FIGURES

The invention will be described with respect to the following drawing figures, in which like numerals represent like features throughout the description, and in which.

DETAILED DESCRIPTION

Figure 1:
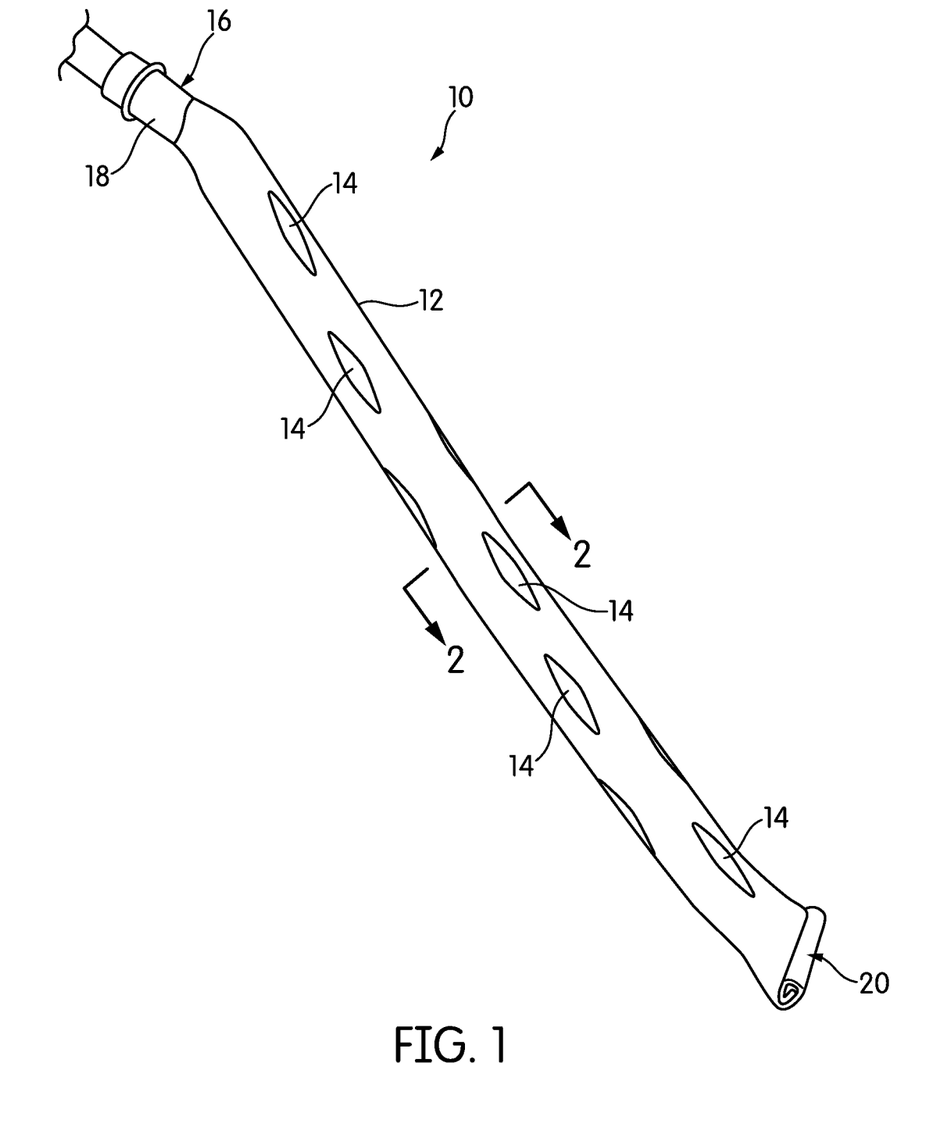
FIG. 1 is a perspective view of a compressible suction device according to one embodiment of the invention.

FIG. 1 is a perspective view of a compressible suction device, generally indicated at 10, according to one embodiment of the invention. The device 10 is elongate and thin with an outer layer 12 that is at least substantially impermeable to liquids. The outer layer 12 has a pattern of perforations 14 along its length. The device 10 has a proximal end 16 with a coupling 18 that is adapted for attachment to suction tubing and, ultimately, a suction pump. The distal end 20 of the device 10 in this embodiment comprises a rolled or crimped section of outer layer 12 material.

The coupling 18 may have specific structure designed to connect with tubing, or it may not. For example, the coupling 18 may include a rigid section adapted to connect with tubing. In some cases, that rigid section may have barbs or other structures adapted to retain or form a seal with tubing, e.g., forming a kind of port or structured coupling for making connections. In other cases, the coupling 18 may simply be an extension of the device 10 that is long enough to connect with tubing, without any particular specialized structure for doing so. In either case, external hardware, such as adapter tubes and clamps, may be used to make connections with the coupling 18.

Figure 2:
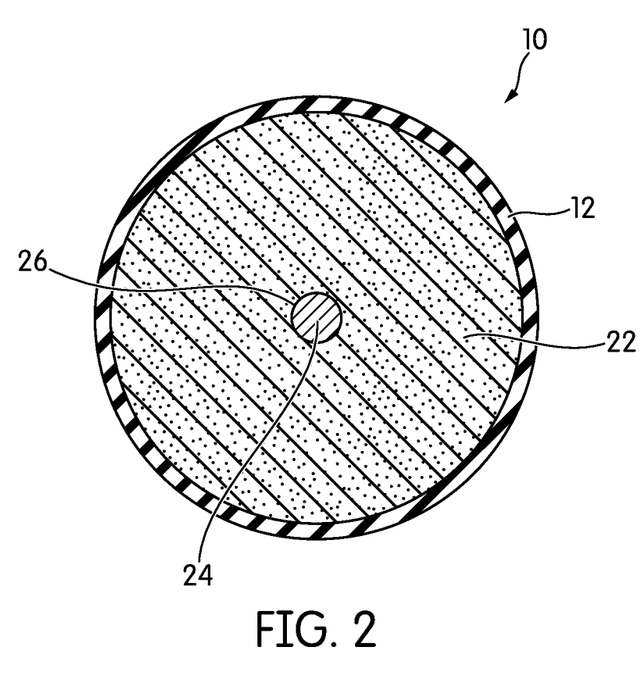
FIG. 2 is a cross-sectional view taken through Line 2-2 of FIG. 1.

FIG. 2 is a cross-sectional view of the device 10, taken through Line 2-2 of FIG. 1. The outer layer 12 may be a latex rubber or a synthetic elastomer of similar properties. Generally speaking, the outer layer is soft and thin. Although the outer layer 12 is shown as a separate element in FIG. 2, in some embodiments, the outer layer 12 may be co-extruded, co-molded, or otherwise joined with the core 22. Additionally, while the outer layer 12 is substantially impermeable to liquids except for its perforations 14 in this embodiment, an outer layer that is more fully liquid-permeable may be used in some embodiments, so long as the outer layer retains its structural integrity when wet and can protect the core 22 from disintegration. An outer layer that is more fully liquid permeable may not require perforations, although it may have perforations or other openings to allow larger particles to migrate to the core more easily. In any case, the outer layer 12 allows liquids and solids to flow selectively into the device 10.

The core 22 of the device 10 of this embodiment is compressible, which, in this context, means that the core 22 will compress when exposed to the kinds of suction pressures applied in medical settings. In this embodiment, the core 22 comprises open-celled foam, e.g., of the type used in negative-pressure wound therapy (NPWT) dressings. The core 22 of this embodiment and the device 10 itself are cylindrical. While the term "foam" is used here for descriptive convenience, any compressible, porous substrate material having an appropriate pore size may be used as a core 22 in embodiments of the invention, whether or not that material is a natural or polymer foam, and the term "foam" should be read broadly to encompass all such materials.

The device 10 also includes a guide wire 24 which, in this embodiment, lies at the geometric center of the device 10, although that need not be the case in all embodiments. The guide wire 24 is typically stiff, malleable, or both, and serves to guide the device 10 during its introduction process into the body, as will be described below in more detail. The guide wire 24, which may be made of a metal, is set within a channel 26 in the core 22 and is arranged such that it can be removed once the device 10 has been introduced. Altogether, the device may have a diameter in the range of 6-10 mm in most embodiments, although larger and smaller embodiments are possible.

Figure 3:
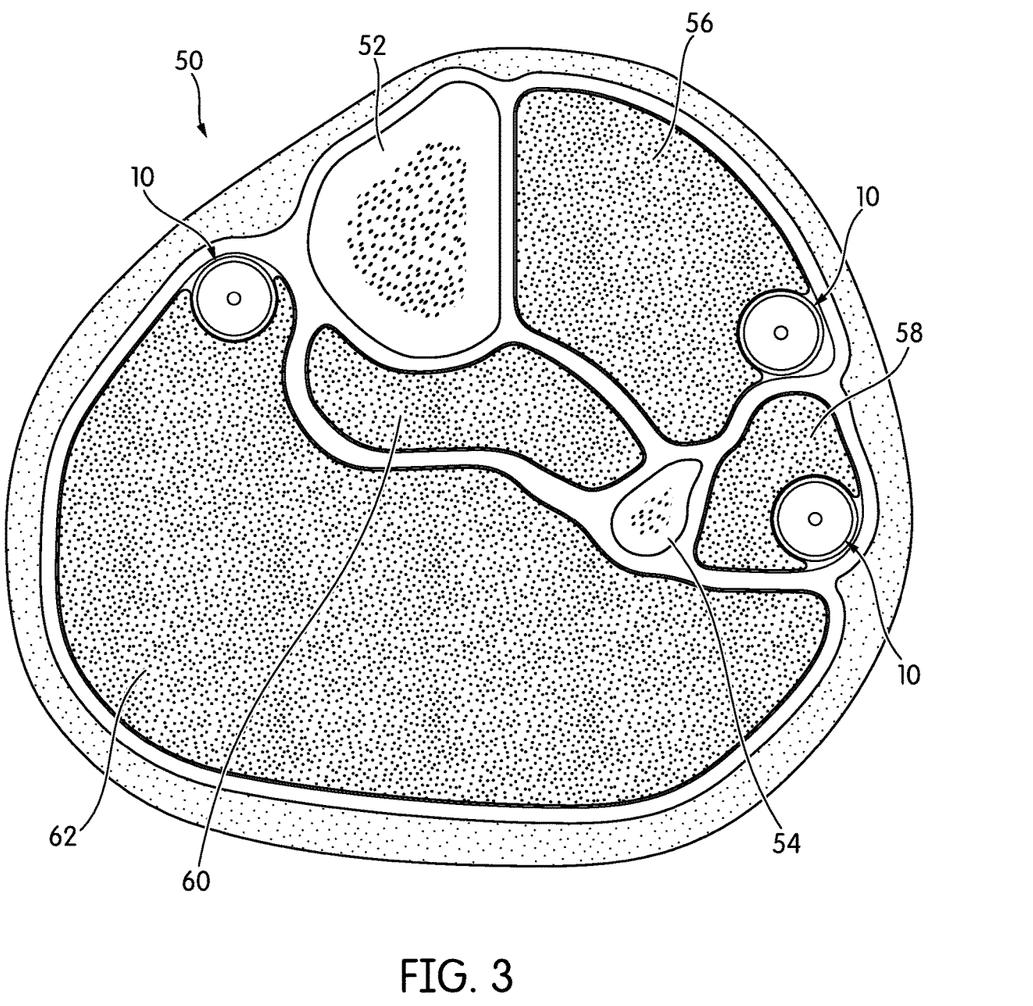
FIG. 3 is a cross-sectional view of the human lower leg, illustrating the tibia, the fibula, and the muscle compartments around those bones, particularly showing the placement of the device of FIG. 1 in the muscle compartments.

The device 10 is particularly adapted to be placed within a muscular compartment and connected to vacuum. In position within the muscular compartment, it may help to prevent compartment syndrome by extracting blood and other fluids that might otherwise build up and increase the intracompartmental pressure. FIG. 3 is a cross-section of the lower leg, generally indicated at 50, showing the positions of the tibia 52, the fibula 54, and the muscle compartments around them, specifically the anterior compartment 56, the lateral compartment 58, the medial compartment 60, and the posterior compartment 62. For purposes of illustration, devices 10 are shown as placed in the anterior compartment 56, the lateral compartment 58, and the posterior compartment 62.

The number of compartments 56, 58, 60, 62 in which devices 10 are placed will depend on the particular patient's case, the nature of the fracture, trauma, or other condition likely to cause or contribute to compartment syndrome, and other factors. In a particular case, it is possible that devices 10 will be placed in only one or two compartments.

Figure 4:
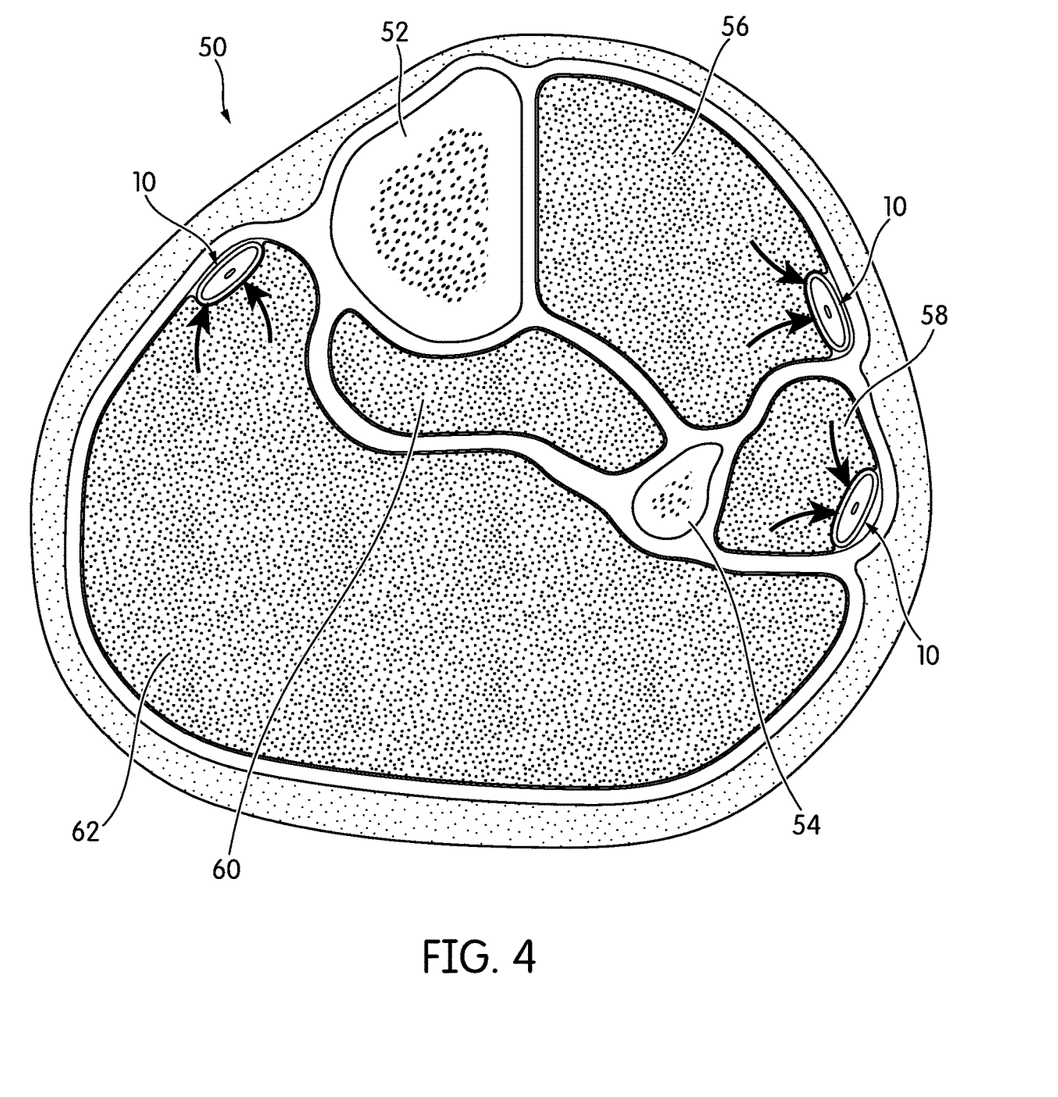
FIG. 4 is a cross-sectional view similar to the view of FIG. 3, illustrating the devices of FIG. 1 with suction applied.

FIG. 4 is a cross-sectional view similar to the view of FIG. 3, illustrating the devices 10 after suction has been applied to their proximal ends 16. As shown, the suction compresses each device 10 and materials in the compartment 56, 58, 62 are drawn into the devices 10 through the perforations 14.

The compressibility of the devices 10 may be advantageous in use. As was described above, the muscular compartments 56, 58, 60, 62 have limited volume and thus limited space for the insertion of devices. The anterior compartment 56 and the lateral compartment 58 are particularly small and particularly prone to compartment syndrome. Yet the application of suction causes the devices 10 to compress, reducing their volume.

Although the devices 10 perform a similar function to that of a traditional suction catheter, their compressibility represents a significant difference between them and a suction catheter. While there have been some attempts to use suction catheters for prevention and treatment of compartment syndrome, these traditional devices have always presented a conundrum: a small-bore catheter often cannot provide enough suction to adequately relieve the pressure, while a large-bore catheter may be too large for the compartment in which it is to be placed, such that its very presence may exacerbate the problem. The compressibility of the devices 10 may allow the devices 10 to provide some of the advantages of a large bore, while having a relatively small cross-section.

Figure 5:
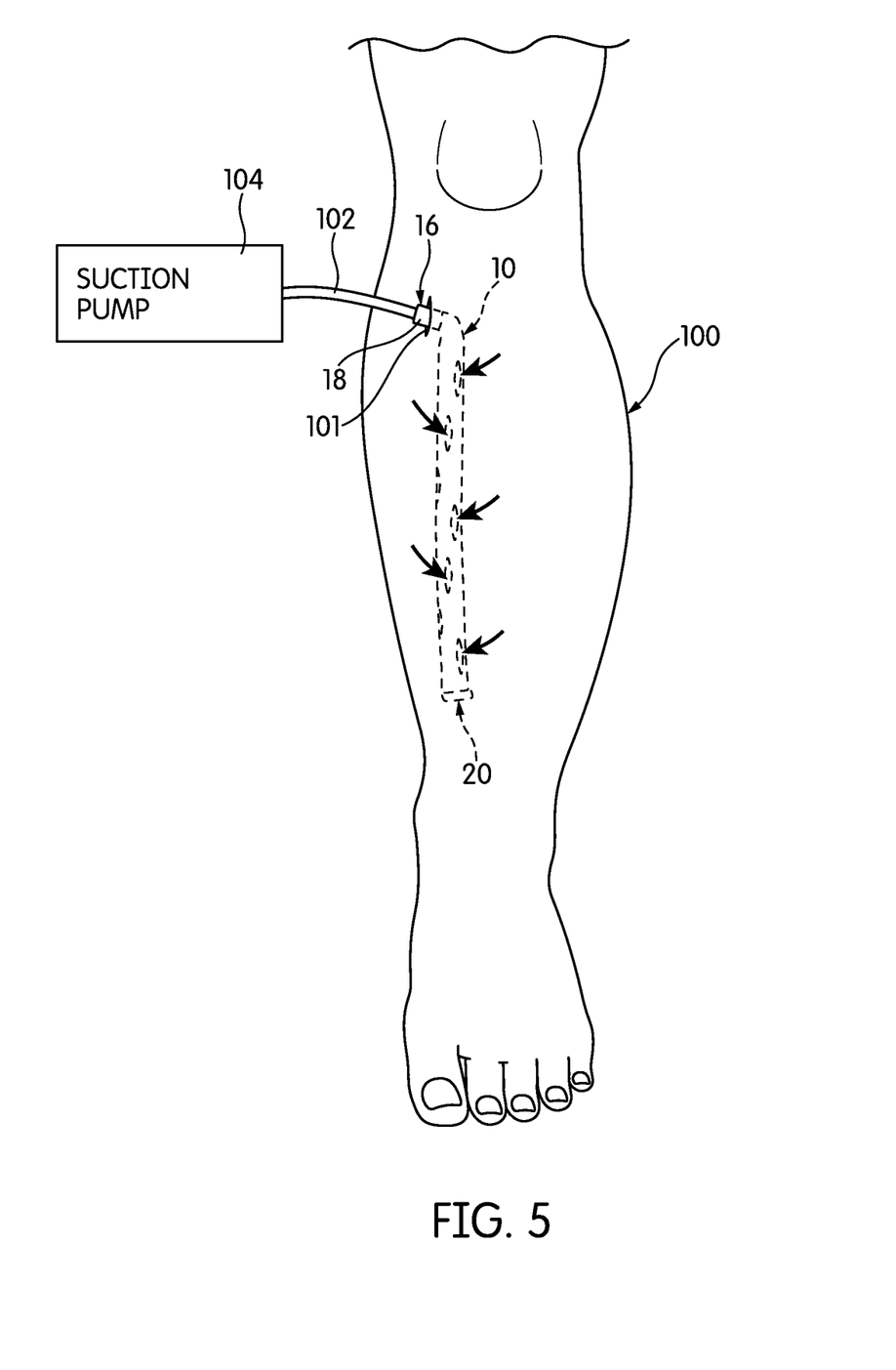
FIG. 5 is a front elevational view of the human lower leg, illustrating the placement of the device of FIG. 1 along a muscle compartment.

FIG. 5 is a front elevational view of a lower leg, generally indicated at 100. In particular, FIG. 5 illustrates a device 10 in position within what, for purposes of the present description, may be assumed to be the anterior compartment 56. As shown, the device 10 is inserted through a small incision 101 and spans substantially the entire length of the compartment 56, with its coupling 18 protruding from the incision 101. The coupling 18 at the proximal end 16 of the device 10 is connected by tubing 102 to a suction pump 104. The device 10 extends in the proximal-to-distal direction along the leg 100; however, in actual use, the device 10 may be inserted in any way that the surgeon sees fit. In particular, it may be inserted through a more distal incision to extend proximally along the leg 100. Additionally, the proximal end of the device 10 may be secured in place using any appropriate technique.

The suction pump 104 may be a local device that is provided for each patient, or the device 10 may be connected to a central vacuum system. If multiple devices 10 are placed in a patient, a single suction pump 104 may service all of the devices 10, or each device 10 may be provided with its own suction pump 104.

Typically, the device 10 would be provided with at least one radio-opaque feature, so that proper placement can be confirmed by X-ray. This radio-opaque feature may be, e.g., a stripe of paint containing a radio-opaque element, such as barium, or a metal ball at the distal end 20 of the device 10.

As the description above bears out, the device 10 is relatively simple in construction. While devices 10 may be manufactured as described, one advantage of the device's simple construction is that, if necessary, a compressible device 10 can be constructed in the operating room during a procedure. For example, a section of commercially available V.A.C.® sponge may be cut to an appropriate size and placed within a casing such as a Penrose drain. The casing would be perforated as needed and, if needed, a guide wire inserted.

Figure 6:
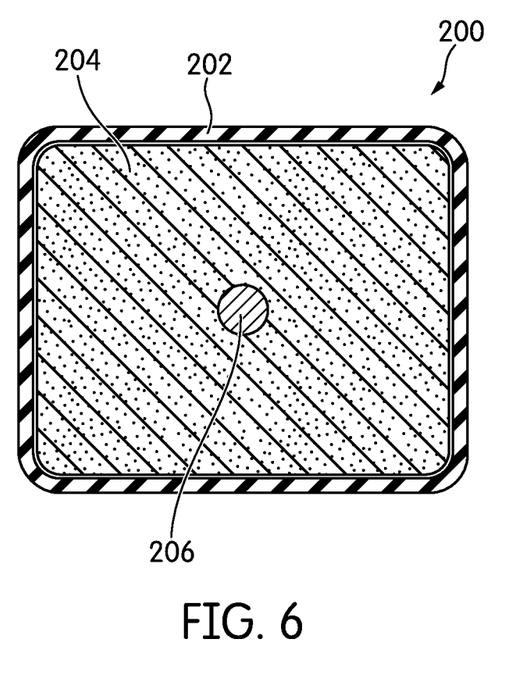
FIG. 6 is a cross-sectional view of a device according to another embodiment of the invention.

The device 10 need not be cylindrical in shape. Devices according to embodiments of the invention may have a variety of shapes and sizes. FIG. 6 is an illustration of a device, generally indicated at 200, according to another embodiment of the invention. Like the device 10, the device 200 has an outer covering 202 that is perforated but otherwise substantially impermeable to liquids. An open-celled foam core 204 lies within the covering 202. A guide wire 206 extends the length of the device 200. However, in contrast to the device 10, the device 200 has a generally rectangular cross-section. The covering 202 also extends more loosely around the core 204 in the view of FIG. 6. This is how a device 200 might appear if it is constructed ad hoc using available materials.

Figure 7:
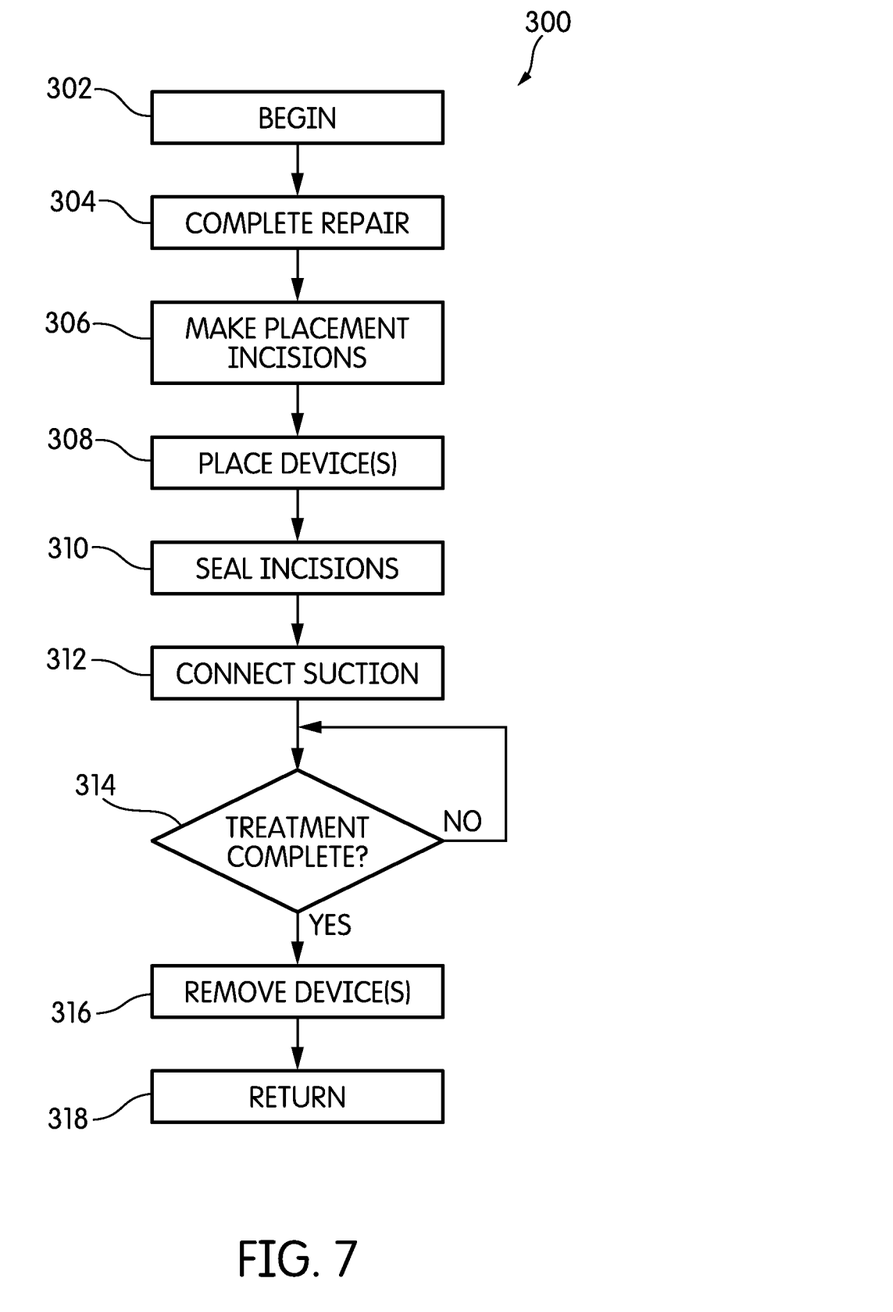
FIG. 7 is a flow diagram of a method for using devices according to embodiments of the invention.

FIG. 7 is a flow diagram of a method, generally indicated at 300, for using devices 10, 200 according to embodiments of the invention. Method 300 begins at 302 and continues with task 304. This description of method 300 assumes that there is an increased risk of compartment syndrome because of trauma to a limb, although in some embodiments, devices 10, 200 may be used even when there has been no trauma, in association with any surgical procedure, event, or set of symptoms likely to raise the possibility of compartment syndrome.

In task 304, the surgeon completes the repair of the traumatic injury or whatever other procedure was undertaken. This may involve a fracture repair, another type of surgical repair, or an elective procedure that would typically raise the risk of compartment syndrome. Method 300 continues with task 306.

In task 306, the surgeon makes incisions to place the devices 10, 200. These incisions would typically be small, on the order of a few centimeters, e.g., 3 cm. In some cases, if the repair or other procedure performed or completed in task 304 requires an appropriately-placed incision, it may not be necessary to make an incision for the devices 10, 200 in task 306. Method 300 continues with task 308.

In task 308, devices 10, 200 are placed. As was described briefly above, this may involve the placement of the devices 10, 200 in any or all of the muscular compartments. In the performance of task 308, the surgeon may use devices 10, 200 sized for the particular muscular compartments, or he or she may cut a device 10, 200 to the desired length in the operating room prior to placement. Once the devices 10, 200 are placed, method 300 continues with task 310.

In task 310, with the devices 10, 200 inserted, the incisions are sealed with standard techniques, such as polymer glues. Method 300 continues with task 312 and suction is applied. The precise pressure that is applied will vary from embodiment to embodiment, but pressures of at least about 125 mmHg may be sufficient in most embodiments. In addition to the external suction pressure applied, the structure of the foam core 22, 204 of the device 10, 200 may create its own capillary suction pressure. Once suction is applied, intracompartmental pressure may be checked using standard devices. Method 300 continues with task 314, a decision task.

Once devices 10, 200 are placed, they are typically left in the patient for some period of time. That period of time is usually a period of time sufficient to ensure that the patient is no longer at greater risk of developing compartment syndrome, e.g., 12 hours, 24 hours, or 48 hours. The devices 10, 200 may be particularly useful at night, when it is usually more difficult to monitor patients for compartment syndrome because of reduced staffing in most hospitals. In some cases, the period of time that the devices 10, 200 remain implanted may be predetermined, based on evidence and best practices. In other cases, the devices 10, 200 may remain implanted until certain clinical signs or metrics are seen. For example, if measured intracompartmental pressure remains below a certain level for a particular period of time, that may indicate that it is safe to remove the devices 10, 200. If the treatment period is not complete or it is desirable to retain the devices 10, 200 in place (task 314: NO), method 300 continues with task 314. When it is time to remove the devices 10, 200, method 300 continues with task 316.

Device removal is indicated at task 316 of method 300. In many cases, the devices 10, 200 can be removed at bedside after disconnecting suction, although X-ray and other techniques may be used to confirm that removal is complete. In case of complications, tearing, or partial removal, a patient may need to be returned to the operating room for complete removal. Method 300 completes at 318.

Of course, the above is a general description of how a device 10, 200 according to embodiments of the invention may be used. The precise use of these devices 10, 200 will vary by situation and will involve the use of surgical judgment. Although much of this description focuses on the use of the described devices 10, 200 secondary to trauma, in some cases, the devices 10, 200 may be used after elective tibial osteotomies, or in the process of revascularizing an ischemic limb, for which prophylactic fasciotomies would typically be performed. Additionally, although this description focuses on the use of the devices 10, 200 in the treatment of humans, devices 10, 200 according to embodiments of the invention may be used in veterinary surgery as well, if indicated. The following example gives a clinical scenario and context in which a device 10, 200 may be used.

Example

A 30-year-old male presents to the Emergency Room after an isolated closed tibia fracture. He presents with full dorsiflexion and plantar flexion of the foot and sensation intact, and is admitted to the hospital with a plan for surgical fixation. The following day, he remains without evidence of neurovascular compromise, and routine tibial nailing is performed. In the operating room, the orthopaedic surgeon recognizes that while the patient does not have compartment syndrome now, he is at risk for it. Further, while he will be checked on regularly overnight, surgeons will not be available in the hospital at night, and the surgeon will remain worried.

The surgeon makes a 3 cm incision in the usual location for a two-compartment fasciotomy. He or she finds the fascial planes and makes an incision over the anterior compartment. He then uses a long pituitary rongeur or another device to implant a device 10, 200 into the anterior compartment, cutting it to length and sealing the distal end 16 as needed. Using the same incision, he identifies the intermuscular septum and places a device in the lateral compartment. Placement is checked using X-ray, and guide wires are removed. Using standard techniques, he seals the opening using the plastic adhesives and connects the device to a VAC machine. 125 mm Hg suction is applied. If desired, the intracompartment pressure is checked with a standard device. The surgeon can leave the operating room knowing that, while compartment syndrome can still occur, it is less likely and less frequent checking may be required.

While the invention has been described with respect to certain embodiments, the description is intended to be exemplary, rather than limiting. Modifications and changes may be made within the scope of the invention, which is defined by the appended claims.

What is claimed is:

1. A device, comprising:
   a thin, elongate member having
   a proximal end and a distal end opposite the proximal end, the proximal end having a coupling constructed and adapted to connect with tubing;
   a porous or perforated compressible outer layer that allows liquids and solids to flow selectively into the device over substantially the entirety of the length of the device from the proximal end to the distal end; and a compressible core within and encased by the outer layer, the compressible core extending along substantially the entirety of the length of the device from the proximal end to the distal end and being structured to allow the liquids and solids to flow therethrough in a direction toward the coupling while the compressible core is compressed.

2. The device of claim 1, wherein the compressible core comprises an open-celled foam.

3. The device of claim 1, wherein the porous or perforated compressible outer layer comprises a perforated, substantially liquid impermeable material.

4. The device of claim 1, further comprising:
a channel for a guide wire defined in the thin, elongate member; and
a guide wire removably inserted into the channel.

5. The device of claim 4, wherein the channel is defined in the compressible core.

6. The device of claim 1, further comprising one or more radio-opaque markers.

7. A method of reducing the risk of or ameliorating compartment syndrome, comprising:
inserting an elongate, thin, compressible device into a muscular compartment, the device including:
a proximal end and a distal end opposite the proximal end, the proximal end having a coupling constructed and adapted to connect with tubing;
a porous or perforated compressible outer layer that allows liquids and solids to flow selectively into the device over substantially the entirety of the length of the device from the proximal end to the distal end; and
a compressible core within and encased by the outer layer, the compressible core extending along substantially the entirety of the length of the device from the proximal end to the distal end and being structured to allow the liquids and solids to flow therethrough in a direction toward the coupling while the compressible core is compressed;
connecting the device to suction; and
retaining the device within the muscular compartment under the suction for a defined period of time.

8. The method of claim 7, further comprising cutting a distal end of the device such that the device has a desired length.

9. The method of claim 7, further comprising removing the device from the muscular compartment after the defined period of time.

10. The method of claim 7, wherein the muscular compartment is in a lower leg.

11. The method of claim 7, wherein the muscular compartment is in an arm.

12. The method of claim 7, wherein the device compresses under the suction.

13. A system, comprising:
a device comprised of a thin, elongate member having
a proximal end and a distal end opposite the proximal end, the proximal end having a coupling constructed and adapted to connect with tubing, the distal end being cuttable such that the device can be cut to a desired length,
porous or perforated compressible outer layer that allows liquids and solids to flow selectively into the device over substantially the entirety of the length of the device from the proximal end to the distal end,
a compressible core comprised of open-cell foam within and encased by the outer layer, the compressible core extending along substantially the entirety of the length of the device from the proximal end to the distal end and being structured to allow the liquids and solids to flow therethrough in a direction toward the coupling while the compressible core is compressed, and
a guide wire removably positioned within the device; and
a suction pump adapted to be connected to the device by the coupling to apply suction pressure to the device.

14. The system of claim 13, wherein the porous or perforated compressible outer layer comprises a perforated, substantially impermeable material.

15. The system of claim 13, wherein the suction pump is adapted to apply at least about 125 mmHg of suction pressure to the device.

16. The system of claim 13, wherein the device compresses under the suction pressure.

* * * * *